United States Patent [19]

Weeks

[11] Plant 4,048

[45] May 3, 1977

[54] ROSE PLANT

[76] Inventor: O. L. Weeks, 926 W. Philadelphia, Ontario, Calif. 91761

[21] Appl. No.: 693,791

[22] Filed: June 7, 1976

[51] Int. Cl.[2] ..... A01H 5/00

[52] U.S. Cl. ..... Plt./3

[58] Field of Search ..... Plt./3

*Primary Examiner*—Robert E. Bagwill

*Attorney, Agent, or Firm*—Frank B. Robb

EXEMPLARY CLAIM

1. A new and distinct variety of rose plant of the climbing class, substantially as herein shown and described, characterized particularly as to novelty by the long, extremely strong and vigorous canes which attain an average mature height of 6 to 8 feet, the habit of bearing its flowers on stems which grow as laterals from the climbing canes, and the long life of the flowers both on the plant and when cut.

1 Drawing Figure

The present invention relates to a new and distinct variety of rose plant of the climber class, which was discovered by me as a sport on an asexually reproduced seedling, which seedling was itself the result of breeding of the rose variety known as "Arlene Francis" (U.S. Plant Pat. No. 1,684) with an unnamed and unpatented seedling which I designate in my records as No. 604-17, the seedling upon which this sport was discovered being identified as No. 6951-1.

The seedling upon which this sport was discovered is disclosed in detail in my co-pending application Ser. No. 693,737 directed to the seedling which I have identified above.

This sport was discovered by me in a routine inspection of a block of plants of the seedling described above, and identified by me as No. 6951-1, which had been asexually reproduced by budding in Ontario, Calif.

My new variety disclosed herein, is particularly characterized by its vigorous climbing canes which come with 6 to 8 foot height, the flowers being substantially identical with the flowers of the variety which I have referred to, (No. 6951-1) upon which it was discovered, and the other characteristics likewise being the same except for the climbing habit and for the fact that the flowers are produced on stems that grow as laterals from the climbing canes.

My new variety is particularly distinguished as to features and characteristics which I have determined are fixed and transmissible by asexual reproduction, and as far as I know the parent plant (the seedling No. 6951-1) has not disclosed any tendency to effect a climbing habit of growth; thus clearly distinguishing the instant variety from that of the seedling upon which it was discovered.

Although the climbing habit and manner of production of blooms on laterals are the primary characteristics which distinguish this variety from the parent seedling upon which it was discovered, these and other characteristics of my new variety distinguish the same from all other rose varieties of which I am aware, as evidenced by the following unique combination of characteristics which are outstanding:

1. The long, extremely strong and vigorous canes which attain an average mature height of 6 to 8 feet;
2. The habit of bearing its flowers on stems which grow as laterals from the climbing canes;
3. The well formed buds that come in large measure on single stems;
4. The excellent petal substance which provides long life to the flower, both on the plant and when cut; and
5. Its vivid yellow coloring which holds well throughout the life of the flower.

Asexual reproduction of my new variety by budding at Ontario, Calif., shows that the aforementioned characteristics and distinctions come true to form and are established and transmitted through succeeding propagations.

The accompanying drawing shows a typical specimen of the vegetative growth of my new variety, and the same is compared in the drawing with a seedling variety identified as No. 6951-1 in my records, and upon which the variety hereof was discovered by way of comparison and to disclose the distinctions of the climbing habit and manner of production of flowers as being typical hereof.

Following is a detailed description of my new variety particularly directed to the climbing habit thereof, but incidentally referring to certain color which is described in my copending application, there being no claim in this application to color of the flowers:

Type: Hardy; climber; outdoor; seedling; for cut flowers and for garden decorations.

Class: Climber.

Breeding: Discovered as a sport on variety I identify as No. 6951-1.

Propagation: Holds its distinguishing characteristics through successive propagation by budding.

FLOWERS

Locality where grown and observed: Ontario, Calif.

Flowers borne: Several to a stem in regular, pyramidal clusters on normally strong, medium to long length stems.

Quantity of bloom: Free and abundant, outdoors and in greenhouse.

Continuity: Continuous.

Fragrance: Slight.

PLANT

Foliage:

*Leaves.*—Compound of five leaflets; normally abundant; medium size; soft; leathery; semi-glossy.

*Leaflets.*— Shape — Obovate, with apex acute, with margin irregularly serrate.

*Rachis (the supporting stem of the compound leaf)*-.—Light weight. Upper side—Smooth mostly, slightly grooved. Under Side — Moderately smooth.

*Stipules.*—Medium long; medium width; points of average length turning out at an angle of less than 45°.

Disease and insect resistance: No evidence of blackspot and good resistance to powdery mildew and rust as well as rose insects.

Growth:

*Habit.*—Tall 6 to 8 feet, much branched.

*Growth.*—Vigorous.

Canes.—Long, extremely strong vigorous canes, attaining an average mature height of 6 to 8 feet.

*Main stems.*—Large prickles — Many; long; straight, slightly downward with narrow base. Small prickles — Few. Hairs — None.

Flowers on stems grow as laterals from the climbing canes.

I claim:

1. A new and distinct variety of rose plant of the climbing class, substantially as herein shown and described, characterized particularly as to novelty by the long, extremely strong and vigorous canes which attain an average mature height of six to eight feet, the habit of bearing its flowers on stems which grow as laterals from the climbing canes, and the long life of the flowers both on the plant and when cut.

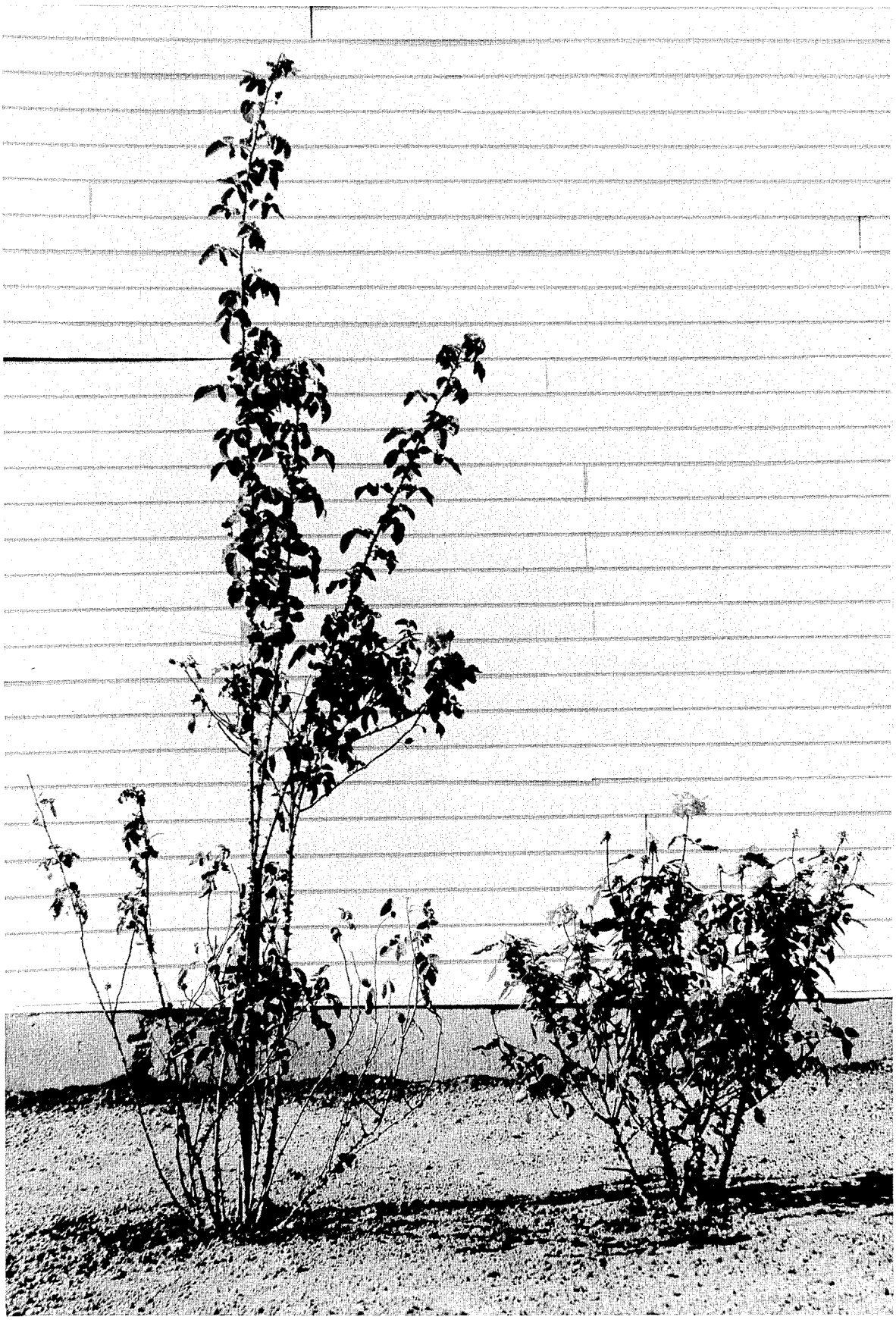

* * * * *